United States Patent [19]

Schouten

[11] Patent Number: 4,500,738
[45] Date of Patent: Feb. 19, 1985

[54] PREPARATION OF ALKOXY METHYL ETHERS

[75] Inventor: Henry G. Schouten, West Chester, Pa.

[73] Assignee: American Home Products Corporation, New York, N.Y.

[21] Appl. No.: 560,011

[22] Filed: Dec. 8, 1983

[51] Int. Cl.³ .................. C07C 41/14; C07C 45/64
[52] U.S. Cl. ................... 568/433; 568/315; 568/592
[58] Field of Search ............. 568/315, 433, 592

[56] References Cited

U.S. PATENT DOCUMENTS 3,928,626 12/1975 Yardley et al. .............. 424/330
3,987,105 10/1976 Yardley ...................... 568/433

OTHER PUBLICATIONS

Edwards et al., Jour. Chem. Soc., (1967), 411–413.
Fujii et al., Synthesis, (1975), 276–277.
Yardley et al., Synthesis, (1976), 244.
Olah et al., Synthesis, (1981), 471–472.
Schaper, Synthesis, (1981), 794–796.

Primary Examiner—Bernard Helfin
Attorney, Agent, or Firm—Richard K. Jackson

[57] ABSTRACT

Alkoxymethyl protecting groups for organic hydroxyl substituents may be introduced into the desired compounds by acetal exchange between an alkylal and an alcohol in the presence of phosphorus oxychloride and dimethylformamide.

5 Claims, No Drawings

PREPARATION OF ALKOXY METHYL ETHERS

BACKGROUND OF THE INVENTION

Organic hydroxyl substituents are advantageously protected during chemical reactions as alkoxy methyl ethers. One example of such protection is seen in the preparation of Ciramadol in U.S. Pat. No. 3,928,626. These ethers are conventionally produced in small quantities by reaction of a molar excess of chloromethyl ether ($CH_3OCH_2Cl$) with a phenolic hydroxyl group at reflux temperature in dry acetone and in the presence of a large excess of anhydrous potassium carbonate. Edwards et al., J. Chem. Soc., 1967, pp. 411–413 (Experimental). The preparative procedure is not desirable in commercial or pilot plant scale production of protected phenols because chloromethyl ether is extremely carcinogenic.

To avoid use of chloromethyl ether in the production of protected hydroxyl groups, various techniques have been developed, each of which presents its own processing disadvantages. For example, Fuji et al., Synthesis (1975) 276, report upon a method for introduction of the methoxymethyl protecting group involving the reaction of methylal(dimethoxymethane) with an alcohol in the presence of phosphorus pentoxide. This method is undesireable because on a production scale above that employed in the laboratory, the handling of insoluble phosphorus compounds (two moles of phosphorus pentoxide is employed for each mole of the hydroxy compound) becomes a major problem.

Yardley et al., Synthesis (1976) 244, modified the acid catalyst in the acetal exchange reaction by using p-toluene sulfonic acid as the acid catalyst and a molecular sieve to remove methanol as a azeotrope with dichloro methane, thereby driving the reaction toward completion and a respectable yield. This procedure, in addition to the disadvantage of a molecular sieve for methanol removal, required extended reaction times of up to about forty-eight hours to obtain a satisfactory yield. Olah et al., Synthesis (1981) 471, further modified the acid catalyzed acetal exchange reaction by using a perfluorinated solid superacidic Nafion-H catalyst to avoid the tedious aqueous basic work-up conditions of the previously mentioned procedures. This procedure otherwise offers no commercial advantage.

In lieu of methylal as the reactant, ethylal (diethoxymethane) has been used to afford ethoxymethyl ether groups in protection of organic hydroxyl substituents. This procedure, requiring an effective fractionating column to separate the ethanol formed during the process and to drive the reaction toward completion, is illustrated by Schaper, Synthesis (1981) 794.

DESCRIPTION OF THE INVENTION

In accordance with this invention there is provided a process for the production of alkoxymethyloxy ethers in which the alkoxy group contains one or two carbon atoms which comprises reacting an alkylal with a phenolic hydroxy group in the presence of dimethylformamide and phosphorus oxychloride. The acetal exchange will proceed in the absence of dimethylformamide over an extended period of time to yield the desired products in addition to polymeric material. Hence, it is much preferred to conduct the reaction in the presence of dimethylformamide.

The process of this invention is rapidly performed to provide excellent yields of the desired protected alcohols without use of cumbersome workup procedures, special absorbents or other special equipment which were mandatory in the prior art preparatory procedures.

The compound to be protected is generally dissolved in a mixture of the alkoxymethyl ether, an appropriate aprotic, organic solvent such as toluene, heptane or hexane and dimethylformamide. This solution is heated to about 50° C. at which point phosphorus oxychloride is added with vigorous stirring at such a rate that a gentle reflux is maintained. Heating is continued until a sample of the reaction mixture shows that practically all starting material has been converted as established by thin layer chromatography. The reaction time varies from about 1 hour to a maximum of about 4 hours. After the reaction is finished, stirring is stopped and the top layer may be syphoned off from the insoluble dimethylformamide-phosphorus oxychloride complex into an aqueous sodium hydroxide solution, or an aqueous sodium hydroxide solution may be added to the reaction mixture with cooling. After separating the layers, the organic extract is washed with salt water until neutral pH. The organic extract is then concentrated under vacuum to constant weight. This concentrate is generally sufficiently pure to be used as is. Obviously if a highly purified material is required the concentrate may be subjected to a high vacuum distillation.

As is illustrated in the following examples this process is well suited for commercial scale preparations.

EXAMPLE 1

To a mixture of 300 ml toluene, 150 ml methylal and 40 ml dimethylformamide 50 g m-hydroxybenzaldehyde was added and stirred until solution was affected. The solution was heated under nitrogen atmosphere to 65° C. and via an addition funnel 60 ml phosphorus oxychloride was added at such a rate that gentle reflux was maintained. The mixture was heated for a total of 2 hours at which time the temperature had been allowed to reach to 90° C. The toluene layer was poured in 300 ml ice water containing 50 ml 50% sodium hydroxide. The two layers were separated and washed with 2×250 ml saturated salt solution. A small amount of acetic acid was added to the wash to affect a neutral pH. The toluene layer was dried over magnesium sulfate, filtered and concentrated to constant weight under vacuum.

Weight of product 61.4 g, Yield 90.3%.

IR identical to authentic material.

TLC showed only one spot and no evidence of starting material.

EXAMPLE 2

To a mixture of 3 L heptane, 3 L methylal and 400 ml dimethylformamide 500 g m-hydroxybenzaldehyde was added and the mixture was stirred at 20°–25° C. until all the solids had dissolved. The solution was heated to 50°–55° C. under a nitrogen atmosphere and via an addition funnel 600 ml phosphorus oxychloride was added, maintaining a reaction temperature of 50°–55° C. After the addition was completed the mixture was heated for 2 hours allowing the temperature to rise to 68° C. The reaction mixture was cooled to 35°–40° C. and the top layer was syphoned into a mixture of 1.5 L ice and 1.5 L water containing 500 ml 50% sodium hydroxide at such a rate that the temperature did not exceed 30° C. The lower residual layer, which was kept at 35°–40° C. to prevent it from solidifying was again extracted with 500 ml heptane and this extract was added to the first one. The two layers were separated and the aqueous layer was washed once with 500 ml heptane. The aqueous layer was discarded and the combined heptane extracts were washed with saturated salt solution until neutral. The organic extract was then concentrated under vacuum to constant weight.

Weight of product 642.6 g, Yield 94.5%.
IR identical to authentic material.
TLC showed only one spot.
Assay by HPLC 98.9%

EXAMPLE 3

To a mixture of 600 ml methylal, 600 ml heptane and 80 ml dimethylformamide, 100 g m-hydroxybenzaldehyde was added and the mixture was stirred until the solids had dissolved. The solution was heated to 50° C. under a nitrogen atmosphere and via an addition funnel 120 ml phosphorus oxychloride was added over 40 minutes. It was stirred for 2 hours allowing the temperature to rise to 68° C. The mixture was cooled to 25° C. and a solution of 200 ml 50% sodium hydroxide in 500 ml ice water was added slowly via an addition funnel allowing the temperature not to exceed 30° C. After the addition was finished, the mixture was basic. The two layers were allowed to settle and then were separated. The aqueous layer was washed with 100 ml heptane and then discarded. The organic extracts were combined and washed with 3×200 ml saturated salt solution at which point the extract had a neutral pH. The organic extract was dried over magnesium sulfate, filtered and concentrated to constant weight under vacuum.

Weight of product 132.7 g, Yield 97.5%.
IR identical to an authentic sample.
Assay by HPLC 97.9%.

EXAMPLE 4

To a mixture of 300 ml ethylal, 300 ml heptane and 40 ml dimethylformamide 50 g m-hydroxybenzaldehyde was added and the mixture was stirred until all solids had dissolved. The solution was heated to 50° C. under a nitrogen atmosphere and via an addition funnel 60 ml phosphorus oxychloride was added over 30 minutes. After the addition was completed, heating was continued for 2 hours allowing the temperature to rise to 70° C. The reaction mixture was cooled to 30° C. and a solution of 250 ml ice water containing 100 ml 50% sodium hydroxide was added over 30 minutes keeping the temperature below 30° C. Gentle stirring was continued for 30 minutes. The two layers were allowed to settle and then separated. The bottom aqueous layer was extracted with 50 ml heptane and discarded. The combined heptane extracts were washed with 3×100 ml salt solution at which point the mixture was neutral. The organic extract was dried over magnesium sulfate, filtered and concentrated to constant weight under vacuum.

Weight of product 67.2 g, Yield 91.0%.
TLC showed only 1 spot, no evidence of the starting material.

EXAMPLE 5

To a mixture of 300 ml methylal, 300 ml heptane and 40 ml dimethylformamide 50 g p-hydroxy acetophenone was added and the mixture was stirred until all solids had dissolved. The solution was heated to 50° C. under a nitrogen atmosphere and 60 ml phosphorus oxychloride was added over 30 minutes at 50°–55° C. The mixture was heated for 2 hours allowing the temperature to rise to 68° C. The reaction mixture was then cooled to 30° C. and a solution of 250 ml ice water containing 100 ml 50% sodium hydroxide was added at such a rate that the temperature of the reaction mixture did not exceed 30° C. After stirring the mixture gently for 30 minutes, the two layers were allowed to settle and were separated. The aqueous layer was washed with 100 ml heptane and discarded. The combined organic layers were washed with 3×200 ml saturated salt solution at which point the pH of the mixture was neutral. The organic extract was dried over magnesium sulfate, filtered and concentrated to constant weight under vacuum.

Weight of the product 55.4 g, Yield 83.7%.
TLC one major spot, no evidence of starting material.

What is claimed is:

1. A process for the production of an alkoxymethyl oxyether of a phenolic hydroxyl group which comprises reacting methylal or ethylal with said phenolic hydroxyl group in the presence of dimethylformamide and phosphorus oxychloride.

2. A process of claim 1 in which methylal is reacted with m-hydroxybenzaldehyde in the presence of dimethylformamide and phosphorus oxychloride.

3. A process of claim 1 in which ethylal is reacted with m-hydroxybenzaldehyde in the presence of dimethylformamide and phosphorus oxychloride.

4. A process of claim 1 in which said process is performed in an aprotic, organic solvent at reflux temperature for a reaction time of from about 1 to about 4 hours.

5. A process of claim 4 in which the reaction time is from about one hour to about 2 hours.

* * * * *